(12) United States Patent
Kim et al.

(10) Patent No.: US 10,034,911 B2
(45) Date of Patent: Jul. 31, 2018

(54) CHONDROCYTE PROLIFERATION PROMOTING AGENT

(71) Applicant: PHARMA FOODS INTERNATIONAL CO., LTD., Kyoto (JP)

(72) Inventors: Mujo Kim, Kyoto (JP); Kazuya Watabe, Kyoto (JP); Jiyeong An, Kyoto (JP); Masayoshi Aosasa, Kyoto (JP); Noriko Horie, Kyoto (JP); Kazuyuki Masuda, Kyoto (JP); Katsuhito Asai, Kanagawa (JP)

(73) Assignee: Pharma Foods International Co., Ltd., Kyoto (JP)

( * ) Notice: Subject to any disclaimer, the term of this patent is extended or adjusted under 35 U.S.C. 154(b) by 0 days.

(21) Appl. No.: 14/412,770

(22) PCT Filed: Jul. 4, 2013

(86) PCT No.: PCT/JP2013/068345
§ 371 (c)(1),
(2) Date: Jan. 5, 2015

(87) PCT Pub. No.: WO2014/007318
PCT Pub. Date: Jan. 9, 2014

(65) Prior Publication Data
US 2015/0164973 A1  Jun. 18, 2015

(30) Foreign Application Priority Data

Jul. 6, 2012  (JP) ................................. 2012-152289
Aug. 23, 2012 (JP) ................................. 2012-183765

(51) Int. Cl.
*A61K 38/01* (2006.01)
*A61K 38/02* (2006.01)
*C12P 21/06* (2006.01)
*A61P 19/02* (2006.01)
*A23L 33/18* (2016.01)

(52) U.S. Cl.
CPC ............ *A61K 38/012* (2013.01); *A23L 33/18* (2016.08); *A61K 38/02* (2013.01); *C12P 21/06* (2013.01); *C12Y 304/00* (2013.01)

(58) Field of Classification Search
None
See application file for complete search history.

(56) References Cited

U.S. PATENT DOCUMENTS

2007/0254040 A1* 11/2007 Scaffidi .................. A61K 35/32
424/550

FOREIGN PATENT DOCUMENTS

| CA | 2037069 | * | 9/1991 |
|---|---|---|---|
| JP | 2001-328919 | | 11/2001 |
| JP | 2009-51849 | | 3/2009 |
| JP | 2010-124755 | | 6/2010 |
| WO | 2006/075558 | | 7/2006 |
| WO | WO 2006/075558 A1 | * | 7/2006 |

OTHER PUBLICATIONS

Machine Translation of WO 2006/075558, Pub. date: Jul. 20, 2006.*
Silva et al., Rheumatology, 2008, vol. 47:1432-1433.*
International Preliminary Report on Patentability dated Jan. 15, 2015 in International (PCT) Application No. PCT/JP2013/068345.
International Search Report dated Jun. 30, 2013 in International (PCT) Application No. PCT/JP2013/068345.

* cited by examiner

*Primary Examiner* — Xiaozhen Xie
(74) *Attorney, Agent, or Firm* — Wenderoth, Lind & Ponack, L.L.P.

(57) ABSTRACT

The present invention provides a novel active ingredient which can be safely used in preventing, ameliorating or treating diseases related to the cartilage such as cartilage damages and cartilage disorders. Since the egg yolk protein hydrolyzate has an effect on chondrocyte proliferation promotion, it is useful as an active ingredient for preventing, ameliorating or treating cartilage disorders and for preventing, ameliorating or treating joint pain. The egg yolk protein hydrolyzate is a natural-origin material with high safety and, therefore, can be widely used in foods and drinks, medicines, feeds and the like which can be daily ingested.

17 Claims, 3 Drawing Sheets

{Figure 1}
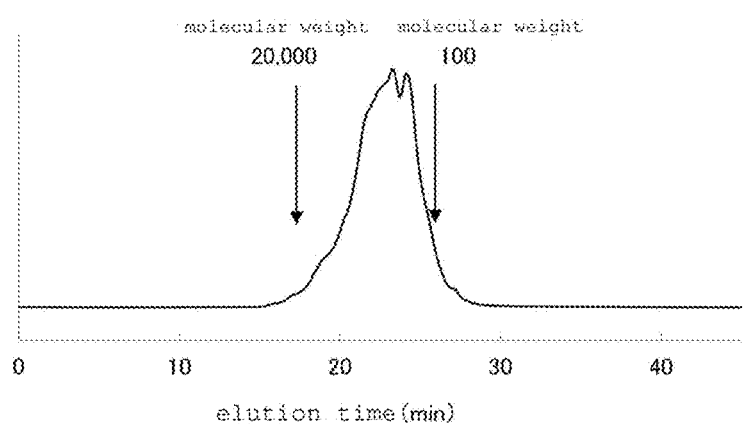
{Figure 2}
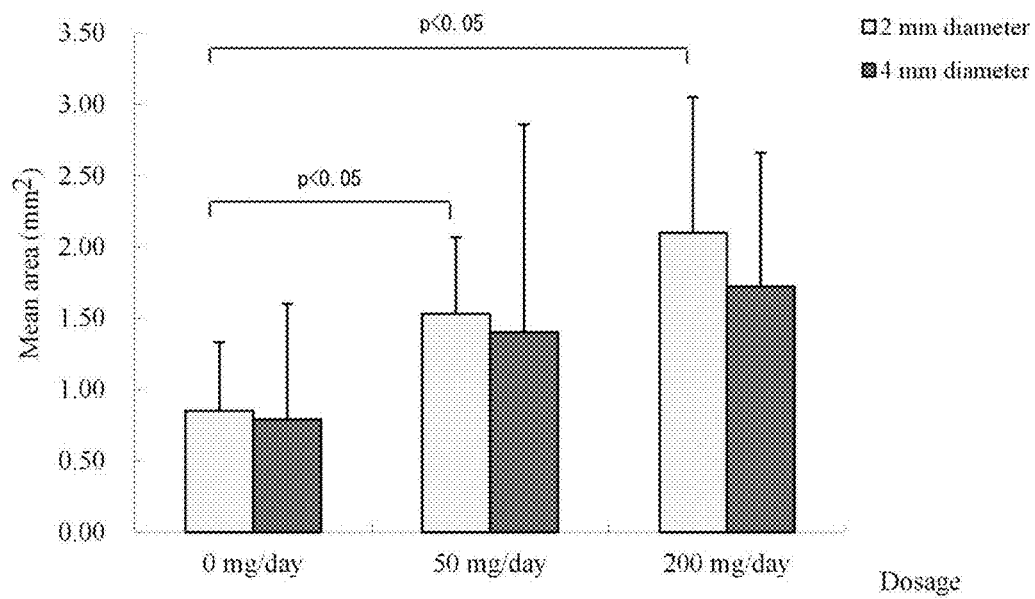

{Figure 3}
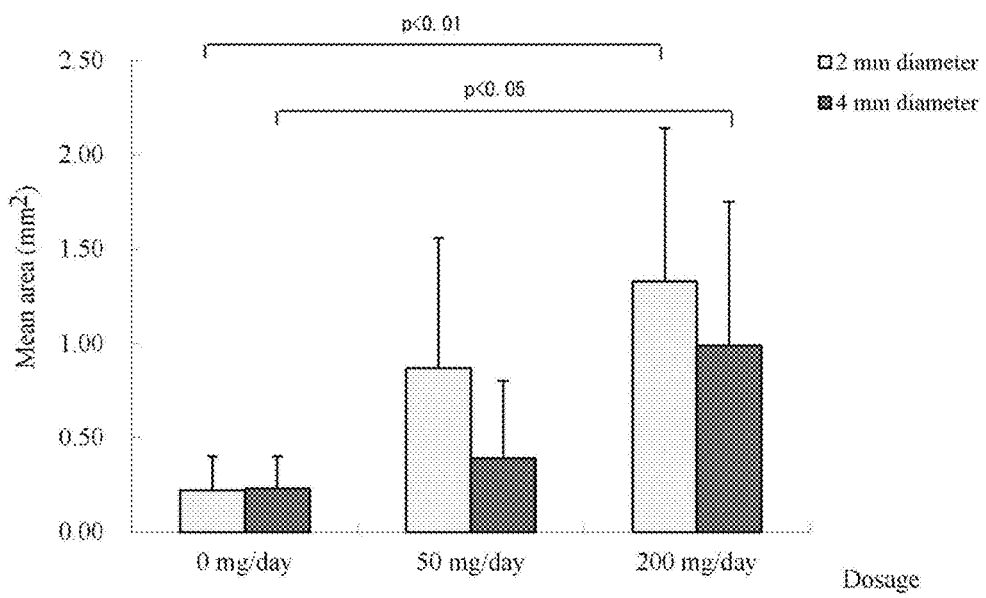
{Figure 4}
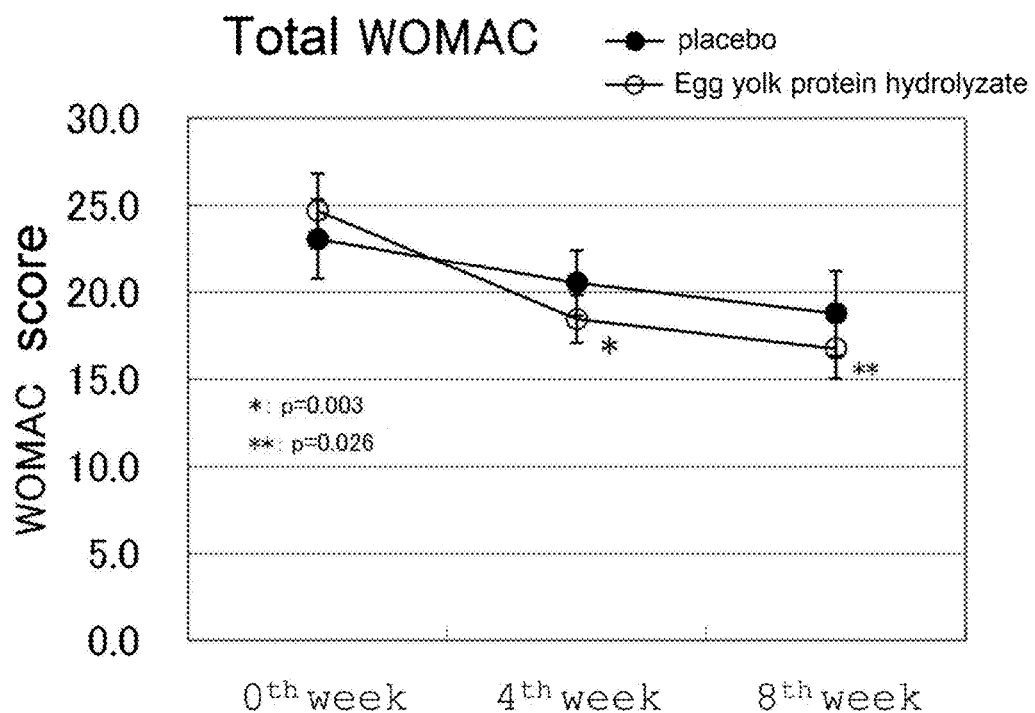

{Figure 5}
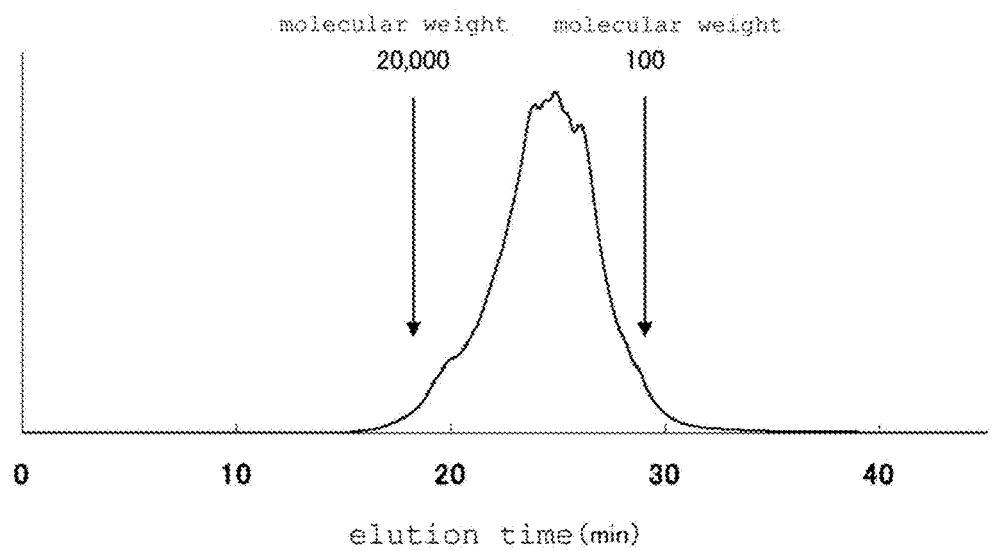
{Figure 6}
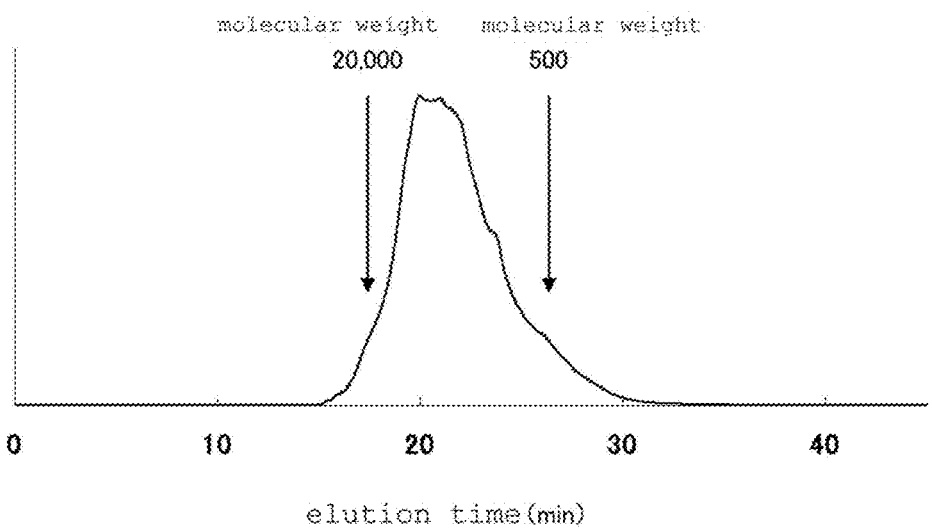

CHONDROCYTE PROLIFERATION PROMOTING AGENT

TECHNICAL FIELD

This invention relates to chondrocyte proliferation promoting agent, preventing or ameliorating agent for cartilage disorders, and preventing or ameliorating agent for diseases related to the cartilage of joint pain and the like, and is particularly directed to chondrocyte proliferation promoting agent, preventing or ameliorating agent for cartilage disorders, and preventing or ameliorating agent for diseases related to the cartilage such as joint pain including the egg yolk protein hydrolyzate as an active ingredient.

BACKGROUND ART

Chondrocyte proliferation and expression of differentiated function are important in the process of prevention and treatment of various cartilage diseases. In other words, it is believed that the proliferation and maturation of chondrocytes lead to the normal growth of bones and the restoration in the case of fracture. TGF-$\beta$1 (Transforming Growth Factor), IGF-1 (Insulin-like Growth Factor), bFGF (basic Fibroblast Growth Factor), PTHrP (PTH-related peptide: parathyroid hormone-related protein), HGF (Hepatocyte Growth Factor), BMP (bone morphogenetic protein), etc. have been reported as factors to induce the proliferation of chondrocytes. However, clinical application of chondrocyte proliferation promoting agent with excellent safety, stability and efficacy has not been established.

The disease with a highest number of patients is osteoarthritis in the cartilage diseases. Aging is considered to be one of the causes, and the increase of the said disease is expected in the aging society in the future. Although bone resorption inhibitory substances such as estrogen and calcitonin, aspirin and non-steroidal anti-inflammatory agents (NSAID) have been conventionally used for the prevention and treatment of cartilage disorders in which cartilage degeneration such as joint diseases is the main lesion, they have never shown sufficient effects and in addition even adverse effects such as gastrointestinal disorders are well known. Therefore, preventing or ameliorating agent safely used in the treatment of cartilage damages and cartilage disorders has been strongly required.

On the other hand, inventors of the present invention have studied the function of the egg yolk protein hydrolyzate, and have found an antioxidant effect (Patent Literature 1), and a bone strengthening effect (Patent Literature 2) and the like. However, effects on cartilage have not been reported.

CITATION LIST

Patent Literature

{PL 1} Japanese Patent Publication No. 2001-328919
{PL 2} International Publication No. WO2006/075558

SUMMARY OF INVENTION

Technical Problem

The present invention aims to provide novel active ingredients which can be safely used for preventing, ameliorating, or treating diseases related to cartilage such as cartilage damages and cartilage disorders.

Solution to Problem

The present invention encompasses the following inventions to solve the above problems.
[1] A chondrocyte proliferation promoting agent characterized by containing the egg yolk protein hydrolyzate as an active ingredient.
[2] A preventing or ameliorating agent of cartilage disorder and/or joint pain characterized by containing the egg yolk protein hydrolyzate as an active ingredient.
[3] A medicament for the prevention or treatment of cartilage disorder and/or joint pain, which comprises a chondrocyte proliferation promoting agent described in the above [1].
[4] A supplement for the prevention or amelioration of cartilage disorder and/or joint pain, which comprises a chondrocyte proliferation promoting agent described in the above [1].
[5] A food additive for the prevention or amelioration of cartilage disorder and/or joint pain, which comprises a chondrocyte proliferation promoting agent described in the above [1].
[6] A use of the egg yolk protein hydrolyzate for the manufacture of chondrocyte proliferation promoting agent.
[7] A use of the egg yolk protein hydrolyzate for the manufacture of a preventing or ameliorating agent of cartilage disorder and/or joint pain.
[8] A method of preventing or ameliorating cartilage disorder or joint pain characterized by orally administering the egg yolk protein hydrolyzate to human in need of promoting chondrocyte proliferation.
[9] A manufacturing method of chondrocyte proliferation promoting agent characterized by comprising a step of defatting egg yolk, a step of obtaining the egg yolk protein hydrolyzate by hydrolyzing the resulting defatted egg yolk with a proteolytic enzyme, and a step of comprising the resulting the egg yolk protein hydrolyzate as an active ingredient.

Advantageous Effects of Invention

The present invention can provide a chondrocyte proliferation promoting agent, a preventing or ameliorating agent of cartilage disorder, and a preventing or ameliorating agent of joint pain. The egg yolk protein hydrolyzate is a natural-origin material with high safety and, therefore, can be widely used in foods and drinks, medicines, feeds and the like which can be daily ingested.

BRIEF DESCRIPTION OF THE DRAWINGS

FIG. 1 is a chart showing the results of mass analysis by gel filtration chromatography on the egg yolk protein hydrolyzate prepared in Example 1.

FIG. 2 is a graph showing a comparison result between the Alcian blue stained area after staining paraffin sections with Alcian blue at the treated knee joint defect portion in the rabbit cartilage defect model and the area in the control group.

FIG. 3 is a figure showing a comparison result between the Safranin O stained area after staining paraffin sections with Safranin O at the treated knee joint defect portion in the rabbit cartilage defect model and the area in the control group.

FIG. 4 is a graph showing the results of examining the effect of ameliorating pain in patients with knee pain by administering the egg yolk protein hydrolyzate.

FIG. 5 is a chart showing the results of mass analysis by gel filtration chromatography on the egg yolk protein hydrolyzate prepared in Example 1.

FIG. 6 is a chart showing the results of mass analysis by gel filtration chromatography on the fractions after fractionating the egg yolk protein hydrolyzate prepared in Example 1.

DESCRIPTION OF EMBODIMENTS

The present invention provides chondrocyte proliferation promoting agent, preventing or ameliorating agent of cartilage disorder and/or joint pain comprising the egg yolk protein hydrolyzate as an active ingredient.

The egg yolk protein hydrolyzate includes, but is not limited to, those obtained by hydrolyzing egg yolk protein are preferable. Egg yolk used as the raw material of the egg yolk protein hydrolyzate includes egg yolk of chicken, duck, quail, etc., but chicken egg yolk is preferably used from the viewpoint of productivity. Egg yolk mixture, egg yolk powder, and defatted egg yolk powder can be used as egg yolk, but egg yolk powder and defatted egg yolk powder is preferably used. Further, from the viewpoint of cost and effective utilization of resources, the use of defatted egg yolk produced as a byproduct during the production of egg yolk oil and egg yolk lecithin from egg yolk is preferred. In the defatting process of egg yolk, treating egg yolk with the organic solvents that can be used in food processing in the egg yolk (e.g., at least one from ethanol, isopropanol, and hexane) is preferable. Ethanol is preferably used from the viewpoint of convenience and safety.

Preferable proteolytic enzymes used for the hydrolysis of egg yolk protein include, but not limited to, enzymes with protease activity or carboxypeptidase activity which can be used for food production. Such examples include pepsin (EC.3.4.23.1), trypsin (EC.3.4.21.4), renin (EC.3.4.23.15), rennet including rennin for cheese, carboxypeptidase A (EC.3.4.17.1), proteases derived from Bacterium of genus *Bacillus* (trade name "Alcalase" Novozymes Inc., trade name "Orientase 22BF" HBI Enzymes Inc., trade name "Nukureicin" HBI Enzymes Inc., trade name "Protease S "Amano" G" Amano Enzyme Company, Ltd., trade name "thermoase PC10" Daiwa Kasei Co., Ltd., etc.), protease derived from Bacterium of genus *Aspergillus* (trade name "Orientase ONS" HBI Enzymes Inc., trade name "Orientase 20A" HBI Enzymes Inc., trade name "Protease P "Amano" 3G" Amano Enzyme Inc.," trade name "Flavourzyme" Novozymes Inc., etc.). The proteolytic enzyme can be used in only one type or in combination of two or more types. The protease derived from Bacterium of genus *Bacillus*, pepsin or a combination thereof is preferable.

The concentration of proteolytic enzymes varies appropriately depending on raw egg yolk and the enzyme used, but in the case of using the defatted egg yolk as a raw material, the mass ratio of the enzyme to the defatted egg yolk is preferably in the range of about 1:20 to about 1:1000. Furthermore, the reaction time enzyme reaction temperature varies depending on raw egg yolk and the enzyme used, but hydrolysis can be preferably carried out at about 25 to about 75° C. for about 1 to 24 hours.

The resulting egg yolk protein hydrolyzate can be used as it is after desalting appropriately. They can be also used after fractionation and purification by a method using ultrafiltration membranes, gel filtration, various column chromatography membrane filters, and the method utilizing the isoelectric point. The egg yolk protein hydrolyzate after purification and fractionation has a chondrocyte proliferation promoting activity, which can be confirmed with reference to the method described in Example 2, for example.

In the resulting egg yolk protein hydrolyzate, the ratio of area in the portion from the molecular weight about 100 or more to about 20,000 or less against the total area of proteins, peptides and amino acids in the molecular weight distribution analysis by gel filtration chromatography is preferably 65% or more, more preferably 75% or more in the said area ratio, further preferably 85% or more in the said area ratio, and further more preferably 90% or more in the said area ratio.

Further, a more preferable egg yolk protein hydrolyzate include a egg yolk protein hydrolyzate obtained by fractionation using an ultrafiltration membrane having a molecular weight of 1,000 wherein the ratio of area in the portion of the molecular weight about 500 or more to about 20,000 or less against the total area of proteins, peptides and amino acids is about 85% or more, preferably about 90% or more in the molecular weight distribution analysis by gel filtration chromatography.

Since the egg yolk protein hydrolyzate obtained in this way has chondrocyte proliferation promoting effect, preventing, therapeutic or ameliorating effect on cartilage disorders, and preventing, therapeutic or ameliorating effect on joint pain, it can be preferably used as an active ingredient of chondrocyte proliferation promoting agent, preventing, therapeutic or ameliorating agent for cartilage disorders, and preventing, therapeutic or ameliorating agent for diseases related to the cartilage such as joint pain. Cartilage disorders include, for example, osteoarthritis, cartilage defect, cartilage damage, injury of semi-lunar disc, and the like.

In chondrocyte proliferation promoting agent, preventing or ameliorating agent of the present invention for cartilage damage and/or joint pain, content of the egg yolk protein hydrolyzate is not particularly limited, but is preferably about 0.05 to about 50 wt %, and more preferably from about 0.1 to about 25 wt %. Further, daily dose of the egg yolk protein hydrolyzate varies with the subject of administration but, for example, in the case of an adult human subject is usually from about 0.05 to about 2000 mg/day, and preferably from about 0.1 to about 1000 mg/day.

The present invention provides a medicament for the prevention or treatment of cartilage disorders and/or joint pain. The medicament of the present invention includes one that contains chondrocyte proliferation promoting agent of the present invention described above. The medicament of the present invention may be administered to a mammal through either oral route or parenteral route. Oral agents include granules, powders, tablets (including sugar-coated tablets), pills, capsules, syrups, emulsions, suspensions, and the like. Parenteral agents include injections (e.g., subcutaneous injections, intravenous injections, intramuscular injections, intraperitoneal injections), drops, external preparations (e.g., preparations for transnasal administration, transdermal preparations, ointments), suppositories (e.g., rectal suppositories, and vaginal suppositories), and the like. These formulations can be prepared by using pharmaceutically acceptable carriers in the conventional methods in the art. The pharmaceutically acceptable carriers include excipients, binders, diluents, additives, flavorings, buffers, thickeners, coloring agents, stabilizers, emulsifiers, dispersing agents, suspending agents, antiseptic agents, etc., and for example, magnesium carbonate, magnesium stearate, talc, sugar, lactose, pectin, dextrin, starch, gelatin, tragacanth, methylcellulose, sodium carboxymethylcellulose, a low melting point wax, cocoa butter and the like can be used as a carrier.

A solid preparation for oral use (tablets, pills, capsules, powders, granules and the like) can be formulated by mixing the active ingredient with excipients (lactose, mannitol, glucose, microcrystalline cellulose, starch, etc.), binders (hydroxypropyl cellulose, polyvinylpyrrolidone, magnesium aluminometasilicate, etc.), disintegrating agents (calcium cellulose glycolate, etc.), lubricants (magnesium stearate, etc.), stabilizers, solubilizing agents (glutamic acid, aspartic acid, etc.) and the like according to conventional methods. They may be coated as needed with coating agents (sugar, gelatin, hydroxypropyl cellulose, hydroxypropyl methyl cellulose phthalate, etc.) and may be coated with two or more layers.

An oral liquid preparation (water agents, suspensions, emulsions, syrups, elixirs, etc.) can be formulated by dissolving, suspending or emulsifying the active ingredient in diluents usually used (purified water, ethanol or a mixture thereof, etc.). Further this liquid preparation may also contain wetting agents, suspending agents, emulsifying agents, sweetening agents, flavoring agents, fragrances, preservatives, buffering agents and the like.

An injection includes solutions, suspensions, emulsions, or solid injections dissolved or suspended in a solvent as needed. The solvents include distilled water for injection, physiological saline, vegetable oil, propylene glycol, polyethylene glycol, alcohols such as ethanol, and mixtures thereof. Further the injection may also contain a stabilizer, solubilizing agents (glutamic acid, aspartic acid, Polysorbate 80, etc.), suspending agents, emulsifying agents, soothing agents, buffering agents, preservatives, and the like. These are prepared by sterilization in the final step or aseptic manipulation. They can be also used by preparing an aseptic solid agent such as freeze-dried products followed by sterilizing prior to use or dissolving in aseptic distilled water for injection or other aseptic solvents.

The present invention provides a supplement for prevention or amelioration of cartilage disorder and/or joint pain. The supplement of the present invention includes one that contains chondrocyte proliferation promoting agent of the present invention described above. The supplement of the present invention may be embodied in the form of an oral solid preparation (tablets, pills, capsules, powders, granules and the like) or an oral liquid preparation. These preparations can be formulated by a procedure similar to the aforementioned medicament.

The present invention provides a food and drink for prevention or amelioration of cartilage disorder and/or joint pain. The food and drink of the present invention includes one that contains chondrocyte proliferation promoting agent of the present invention described above. The food and drink includes health food, functional food, food for specified health use, and food for the sick. The form of food and drink is not particularly limited. It includes, for example, drinks such as tea beverages, soft drinks, carbonated beverages, energy drinks, fruit drinks, and lactic acid drinks; noodles such as buckwheat, udon-noodles, Chinese noodles, and instant noodles; confectioneries and breads such as lollipop, candy, gum, chocolate, snacks, biscuits, jelly, jam, cream, and bakegoods; fisheries and livestock processed food such as fish paste, ham, and sausages; dairy product such as processed milk, and fermented milk; oil and fat processed food such as salad oil, cooking oil, margarine, mayonnaise, shortening, whipped cream, and dressing; seasoning such as a dripping and sauce; retort pouch food such as curry, stew, rice bowl, porridge, and porridge; frozen dessert such as ice cream, sherbet, and shaved ice.

The present invention provides a food additive for the prevention or amelioration of cartilage disorder and/or joint pain. The food additive of the present invention includes one that contains chondrocyte proliferation promoting agent of the present invention described above. Form of the food additive of the present invention is not particularly limited, but includes for example, liquid state, pasty, powdery, flaky, and granular. The food additive of the present invention also includes additives for beverages. Food additive of the present invention can be produced according to the usual manufacturing method of the food additives.

The present invention provides a feed for the prevention or amelioration of cartilage disorder and/or joint pain. The feed of the present invention includes one that contains chondrocyte proliferation promoting agent of the present invention described above. The feed includes, for example, livestock feed for cattle, horse, pig, etc.; poultry feed for chicken, etc.; pet feed for dog, cat, etc. The feed of the present invention can be produced according to the usual manufacturing method of the feed except for adding chondrocyte proliferation promoting agents of the present invention to the feed.

The egg yolk protein hydrolyzate of the present invention, which is the active ingredient for chondrocyte proliferation promoting agent and for the prevention or amelioration of cartilage disorder and/or joint pain, has high safety, mild effects and enabling the administration or use for a long period because it is an ingredient present in egg yolk having rich and long eating experiences. Further, the egg yolk protein hydrolyzate as an active ingredient is a multi-functional component that combines multiple actions and can be expected to have a synergistic or additive effect by using in combination with other active ingredients which are used for treatment of cartilage diseases. The other active ingredients used for treatment of cartilage diseases include, for example, glucosamine, chondroitin, collagen type I, collagen type II, N-acetylglucosamine and the like.

The present invention includes a method of preventing or ameliorating cartilage disorder or joint pain characterized by administering a therapeutically effective amount of the egg yolk protein hydrolyzate to human in need of promoting chondrocyte proliferation. Further it also includes a non-therapeutic method of preventing or ameliorating cartilage disorder or joint pain characterized by orally administering the egg yolk protein hydrolyzate to human in need of promoting chondrocyte proliferation. The term "non-therapeutic" means a concept which does not contain the medical practice, namely treatment acts to a human or animal body.

The present invention includes a manufacturing method of chondrocyte proliferation promoting agent. The manufacturing method of the present invention includes one that contains a step of defatting egg yolk, a step of obtaining the yolk protein hydrolyzate by hydrolyzing the resulting defatted egg yolk with a proteolytic enzyme, and a step of comprising the resulting egg yolk protein hydrolyzate as an active ingredient.

EXAMPLES

The present invention is described below in detail with reference to the following examples, but it should be construed that the invention is in no way limited to those examples.

Example 1: Preparation of the Egg Yolk Protein Hydrolyzate (1) Preparation of Defatted Yolk To 1 kg of egg yolk powder was added 5 L of ethanol. After the mixture was stirred for 30 minutes in a blender, the solid was recovered. This operation was repeated three times for defatting egg yolk and the resulting solid was air-dried to give 568 g of defatted egg yolk powder.

(2) Preparation of the Egg Yolk Protein Hydrolyzate

To 500 g of defatted egg yolk powder obtained in (1) was added 2.5 kg of water and 25 g of Alcalase (trade name, Novozymes Inc., proteases derived from *Bacillus licheniformis*) and then the mixture was subject to adjusting pH 7, enzyme reaction for 3 hours at 55° C., inactivating the enzyme by heat treatment for 15 minutes at 80° C., centrifuging for 20 minutes at 3000×g, and removal of insoluble materials by filtration. The filtrate was spray dried to give about 140 g of the egg yolk protein hydrolyzate.

The obtained egg yolk protein hydrolyzate was analyzed for molecular weight by gel filtration chromatography under the following conditions.

Column: Diol 60 (6.0×300 mm) (trade name, manufactured by YMC)
Eluent: 0.2M potassium phosphate buffer, 0.2M NaCl (pH6.9)/acetonitrile (70:30)
Flow rate: 0.7 ml/min
Detection wavelength: 280 nm The results of molecular weight analysis are shown in FIG. 1. FIG. 1 clearly shows that the yolk protein hydrolyzate of Example 1 has the ratio of area in the portion from the molecular weight about 100 or more to about 20,000 or less against the total area of proteins, peptides and amino acids is about 90%.

Example 2: Examination of Effects on Chondrocyte Proliferation of the Egg Yolk Protein Hydrolyzate The egg yolk protein hydrolyzate prepared in Example 1 was used as the egg yolk protein hydrolyzate.

The cultured cell line derived from mouse embryo cells, ATDC5 (RIKEN BANK, RBC0565), which can differentiate into cartilage-like cells, was used as the cells. ATDC5 seeded at a density of $2\times10^4$ cells/cm$^2$ on 96-well plates was cultured with Eagle's MEM medium containing 5% FCS (bovine fetal serum) under 5% $CO_2$ at 37° C. After incubation for 1 day, the cultured cells were washed once with Eagle's MEM medium without serum and 95 μL of Eagle's MEM medium was added to each well, and after adding 5 μL of the test liquid, the mixture was incubated at 37° C. for 3 days. The test liquid, which was prepared by dissolving the egg yolk protein hydrolyzate in Eagle's MEM medium followed by sterilizing through 0.45 μm filter, was used. The concentration of egg yolk protein hydrolyzate in the test liquid was prepared to be 1 mg/ml or 10 mg/ml at a final concentration when adding 5 μL of the test liquid per well. After culturing for 3 days, the number of cells was counted by MTT method.

The results are shown in Table 1. The number of cells in the group containing the egg yolk protein hydrolyzate was calculated as % value (proliferation value), taking the cell number in the group without containing the egg yolk protein hydrolyzate to be 100%. As shown in Table 1, the egg yolk protein hydrolyzate increases the number of ATDC5 cells in a dose-dependent manner, which shows a proliferation effects on cartilage cells.

TABLE 1

| Final concentration (mg/ml) | Proliferation value (%) |
|---|---|
| 0 | 100 |
| 1 | 111 |
| 10 | 132 |

Example 3: Effect of the Egg Yolk Protein Hydrolyzate Against Rabbit Cartilage Defect Model 3-1 Test Method (1) Test Sample for Administration The egg yolk protein hydrolyzate prepared in Example 1 was used as an egg yolk protein hydrolyzate.

The said egg yolk protein hydrolyzate was prepared to be 50 mg/15 mL (50 mg/day group) and 200 mg/15 mL (200 mg/day group) with purified water and the resulting suspension was used as a test sample for administration.

(2) Test Animal and Test Condition

Rabbits at 22 weeks old are purchased (Slc: JW, SPF, male, Japan SLC, Inc.). After obtained animals were quarantined for 5 days, they were acclimated for a period of 1 day or 7 days. The animals were housed in a breeding room maintained temperature setting at 23° C. and humidity setting at 55%. After obtained animals, they were housed in one per an aluminum cage. They were fed 120 g/day of solid feed (LRC4, Oriental Yeast Co., Ltd.). They had access to water ad libitum.

(3) Preparation of Rabbit Cartilage Defect Model

A mixture of ketamine hydrochloride and xylazine hydrochloride was used for anesthesia with intramuscular administration in thigh muscle. Animals were sheared around the thigh, fixed in the supine position, sterilized with 10-fold dilutions of 5% Hibitane solution (registered trademark, Dainippon Sumitomo Pharma Co., Ltd.), rubbing alcohol, and 10% Isodine liquid, and then administered subcutaneously 2 to 3 mL of lidocaine hydrochloride to the left and right thighs. The outer skin and fascia at right and left thighs were cut with a scalpel to expose the knee joint. The joint capsule was dissected along the inside patellar ligament to dislocate patella. The two bone tunnels at each femoral groove were prepared in a direction perpendicular to the bone surface using drill (Φ2 mm, Φ4 mm). Incidentally, when carrying out the operation, operative field and the bone tunnel were washed with enrofloxacin added (0.05%) saline solution (Otsuka Pharmaceutical Factory). The dissected fascia of the right and left thighs and the skin were sutured using suture (4-0, 3-0 nylon suture, Alfresa Farmer, Inc.). After suturing, Isodin-gel (Meiji Seika Pharma Co., Ltd.) was applied. Enrofloxacin was administered subcutaneously to the back of the neck for two days after surgery. Elizabeth color was mounted for one week after surgery in order to prevent the infection at incision part.

(4) Group Constitution and Test Schedule

Three groups, control group (administration of purified water), 50 mg/day group and 200 mg/day group were set up. Three rabbits per group were used. The gavage administration (15 mL/rabbit) once a day was performed for 3 weeks form the next day of the operation to the day before the autopsy. During the period of administration, the general health condition and the presence of death once a day were observed.

On autopsy date of all cases, after lethal exsanguination from the abdominal aorta under anesthesia with auricular intravenous administration of 4% pentobarbital sodium, the damage site and its surroundings were visually observed at autopsy.

(5) Histopathological Evaluation and Statistical Method

Femur (including the site of injury) was excised and fixed with 4% paraformaldehyde/phosphate buffer solution, and then after defatting, femur was decalcified with K-CX. The center of the defect treatment portion embedded with paraffin according to a conventional method was used as a sample, and thereby HE stained sample, Alcian Blue stained sample and Safranin O stained sample were prepared. The area of stained site was measured using a commercial software (Microsoft Office Excel 2003) in Alcian blue stained sample and Safranin O stained sample.

The mean and standard deviation in Alcian Blue stained area and Safranin O stained area of each group were measured and significant difference test (t-test) was carried out between the control group and 50 mg/day group and between the control group and the 200 mg/day group. The significance level was 5%, and was displayed separately less than 5% ($P<0.05$) and less than 1% ($P<0.01$).

3-2 Results

Death and dying examples in any of the individual cannot be seen, no abnormalities were observed in the general health condition through the administration period. Based on findings in an autopsy at the injury site, it has been observed that the bone hole repairs were progressing both in 50 mg/day group and 200 mg/day group. In particular repair of Φ2 mm bone hole was significantly progressed.

The results of Alcian blue stained area are shown in FIG. 2. As is apparent from FIG. 2, a significant increase was observed in Φ2 mm bone hole in both 50 mg/day group and 200 mg/day group as compared to the control group. This result clearly shows that the oral administration of the egg yolk protein hydrolyzate increases the acidic mucopolysaccharides which are cartilage matrix components.

The results of Safranin O stained area are shown in FIG. 3. As is apparent from FIG. 3, a significant increase was observed in Φ2 mm and Φ4 mm bone holes in 200 mg/day group as compared to the control group. This result clearly shows that the oral administration of the egg yolk protein hydrolyzate increases the acidic proteoglycans which are cartilage matrix components.

Example 4: Effect of the Egg Yolk Protein Hydrolyzate for Patients with Knee Joint Pain 4-1 Test Method
(1) Test Sample The egg yolk protein hydrolyzate prepared in Example 1 was used as an egg yolk protein hydrolyzate. The hard capsule containing 50 mg of the said egg yolk protein hydrolyzate was used as a test sample. A hard capsule (containing vehicle alone) which does not contain the egg yolk protein hydrolyzate was used as a placebo.

(2) The Test Group and the Selection Criteria of the Subjects

For patients with knee joint pain (Average age 56.9 years) selected according to the following selection criteria 1 to 5, the test started with dividing into two groups of the egg yolk protein hydrolyzate-treated group (50 mg/day) and a placebo group.

[Selection Criteria]
1. Patients with subjective symptoms of knee joint pain whose pain is certified by physicians
2. 40 years old to 70 years old
3. People who can come to hospital on the test date
4. People who have no medication for the knee joint
5. Healthy person without mental disease requiring treatment
6. Those briefed on the test and obtained the consent (3) Dosing Period One grain of hard capsule was taken with appropriate amount of water once daily after breakfast in all the groups and was continuously ingested for 8 weeks.

(4) Evaluation

WOMAC (Western Orntario and McMaster Universities Osteoarthritis Index)-questionnaire was used for evaluation. WOMAC is an index that has been used worldwide for subjective pain of osteoarthritis of the knee and subjective physical function, and was fill out by doctors with diagnosing the state on the basis of interview. Evaluation was carried out just before dosing, on the 4th week and on the 8th week. Grouping was conducted so that there is no bias in the evaluation before dosing.

4-2 Results

Results are shown in FIG. 4. The final number of subjects was 16 people and 17 people in the egg yolk protein hydrolyzate administered group and the placebo group, respectively. As apparent from FIG. 4, significant improvement in knee pain was observed in the egg yolk protein hydrolyzate administered group on the 4th week and 8th week after dosing.

Example 5: Molecular Weight Analysis of the Egg Yolk Protein Hydrolyzate

The egg yolk protein hydrolyzate prepared in Example 1 was analyzed for molecular weight by gel filtration chromatography under the following conditions which was different from that in Example 1.

Column: Diol 60 (8.0×500 mm) (trade name, manufactured by YMC)
Eluent: 0.1M potassium phosphate buffer, 0.2M NaCl (pH6.9)/acetonitrile (70:30)
Flow rate: 0.7 ml/min
Detection wavelength: 215 nm The results of molecular weight analysis are shown in FIG. 5. The ratio of area in the portion from the molecular weight about 100 or more to about 20,000 or less against the total area is about 90%.

Example 6: Fractions of the Egg Yolk Protein Hydrolyzate

The egg yolk protein hydrolyzate prepared in the same manner as in Example 1 was fractionated by using an ultrafiltration membrane with a molecular weight of 1,000. The obtained fractions were analyzed for molecular weight by gel filtration chromatography under the same conditions as in Example 5.

The results of molecular weight analysis are shown in FIG. 6. FIG. 6 clearly shows that the ratio of area in the portion from the molecular weight about 500 or more to about 20,000 or less against the total area of proteins, peptides and amino acids is about 90%.

Example 7: Examination of Effects of Fractions on Chondrocyte Proliferation

The effects of fractions on chondrocyte proliferation were examined using the fractions prepared in above Example 6 in the same manner as in Example 2. ATDC5 cells seeded at a density of $2\times10^4$ cells/cm$^2$ on 96-well plates was cultured with Eagle's MEM medium containing 5% FCS under 5%

$CO_2$ at 37° C. After incubation for 1 day, the cultured cells were washed once with Eagle's MEM medium without serum and 95 μL of Eagle's MEM medium was added to each well, and after adding 5 μL of the test liquid, the mixture was incubated at 37° C. for 3 days. The test liquid, which was prepared by dissolving the fractions in Eagle's MEM medium followed by sterilizing through 0.45 μm filter, was used. The concentration of the fractions in the test liquid was prepared to be 1 mg/ml or 10 mg/ml at a final concentration when adding 5 μL of the test liquid per well. After culturing for 3 days, the number of cells was counted by MTT method.

The results are shown in Table 2. The number of cells in the group containing fractions was calculated as % value (proliferation value), taking the cell number in the group without fractions to be 100%. As shown in Table 2, the fractions increases the number of ATDC5 cells in a dose-dependent manner, which shows a proliferation effects on cartilage cells.

TABLE 2

| Final concentration (mg/ml) | Proliferation value (%) |
| --- | --- |
| 0 | 100 |
| 1 | 118 |
| 10 | 145 |

Example 8: Soft Drink

Soft drinks containing the egg yolk protein hydrolyzate prepared in Example 1 were prepared. Namely, after blending the raw material to contain isomerized sugar 15.0%, fruit juice 10%, egg yolk protein hydrolyzate 2.0%, perfume 0.1%, calcium 0.1%, and water 72.8% the mixture was sterilized at 90° C. for 15 seconds by using a plate sterilizer to produce a soft drink.

Example 9: Yogurt

The yoghurt containing the egg yolk protein hydrolyzate prepared in Example 1 was prepared. Namely, after blending the raw material to contain egg yolk protein hydrolyzate 3.0%, sucrose 7%, perfume 0.1%, and yogurt 89.9%, the mixture was filled into a container to produce a yoghurt.

Example 10: Cheese

The processed cheese containing the egg yolk protein hydrolyzate prepared in Example 1 was prepared. Namely, after blending the raw material to contain Gouda cheese 35%, Cheddar cheese 35%, Parmesan cheese 20%, egg yolk protein hydrolyzates 2.0%, calcium phosphate 1.0%, and water 7.0%, the mixture was emulsified at emulsification temperature 85° C. to produce a process cheese.

Example 11: Capsule

After blending the raw material to contain egg yolk protein hydrolyzate prepared in Example 1 60%, corn starch 30%, and 10% lactose, the mixture was filled into a gelatin capsule (200 mg per capsule) to produce a capsule.

Example 12: Tablet

After blending the raw material to contain egg yolk protein hydrolyzate 60% prepared in Example 1 60%, reduced maltose 18%, cellulose 18%, and sucrose ester 4%, the mixture was tableted to produce a tablet.

The present invention is not limited to the embodiments and examples described above, but may be altered within the scope of the claims, and embodiments obtained by combining technical means disclosed in different embodiments appropriately are also included in the technical scope of the present invention.

The invention claimed is:

1. A method of treating or ameliorating joint pain related to articular cartilage comprising orally administering egg yolk protein hydrolyzate to a human in need thereof, wherein the human is suffering from joint pain related to articular cartilage, and wherein the egg yolk protein hydrolyzate is from the retentate fraction of an ultrafiltration using an ultrafiltration membrane with a molecular weight cut-off of 1,000 Daltons.

2. The method of claim 1, wherein the egg yolk protein hydrolyzate has a molecular weight of about 1,000 to about 20,000 Daltons.

3. The method of claim 1, wherein the egg yolk protein hydrolyzate is administered in an amount of about 0.05 to about 2000 mg/day.

4. The method of claim 3, wherein the egg yolk protein hydrolyzate is administered in an amount of about 50 to about 200 mg/day.

5. The method of claim 1, wherein the egg yolk protein hydrolyzate is administered with one or more additional active ingredients selected from the group consisting of glucosamine, chondroitin, collagen type I, collagen type II, and N-acetylglucosamine.

6. The method of claim 1, wherein the egg yolk protein hydrolyzate is administered in an oral solid form or an oral liquid form.

7. The method of claim 6, wherein the oral solid preparation is selected from the group consisting of granules, powders, tablets, pills, capsules, food and food additive.

8. The method of claim 6, wherein the oral liquid preparation is selected from the group consisting of suspensions, emulsions, syrups, elixirs, and beverages.

9. A method of treating or ameliorating joint pain related to articular cartilage comprising administering egg yolk protein hydrolyzate to an animal in need thereof, wherein the animal is suffering from joint pain related to articular cartilage, and wherein the egg yolk protein hydrolyzate is from the retentate fraction of an ultrafiltration using an ultrafiltration membrane with a molecular weight cut-off of 1,000 Daltons.

10. The method of claim 9, wherein the egg yolk protein hydrolyzate has a molecular weight of about 1,000 to about 20,000 Daltons.

11. The method of claim 9, wherein the egg yolk protein hydrolyzate is administered in an amount of about 0.05 to about 2000 mg/day.

12. The method of claim 11, wherein the egg yolk protein hydrolyzate is administered in an amount of about 50 to about 200 mg/day.

13. The method of claim 9, wherein the egg yolk protein hydrolyzate is administered with one or more additional active ingredients selected from the group consisting of glucosamine, chondroitin, collagen type I, collagen type II, and N-acetylglucosamine.

14. The method of claim 9, wherein the egg yolk protein hydrolyzate is administered in an oral solid preparation, a parenteral preparation or an oral liquid preparation.

15. The method of claim 14, wherein the oral solid preparation is selected from the group consisting of granules, powders, tablets, pills, capsules, food and food additive.

16. The method of claim 14, wherein the oral liquid preparation is selected from the group consisting of suspensions, emulsions, syrups, elixirs, and beverages.

17. The method of claim 14, wherein the parenteral preparation is selected from the group consisting of injections, drops, transnasal preparations, transdermal preparations, and suppositories.

* * * * *